United States Patent [19]
Bossert et al.

[11] 3,974,278
[45] Aug. 10, 1976

[54] 1,4-DIHYDROPYRIDINE ESTERS
[75] Inventors: Friedrich Bossert, Wuppertal;
Egbert Wehinger, Neviges; Wulf Vater, Opladen; Kurt Stoepel, Wuppertal, all of Germany
[73] Assignee: Bayer Aktiengesellschaft, Germany
[22] Filed: May 12, 1975
[21] Appl. No.: 576,724

Related U.S. Application Data
[62] Division of Ser. No. 485,300, July 2, 1974, abandoned.

[30] Foreign Application Priority Data
July 12, 1973 Germany.............................. 2335466

[52] U.S. Cl................................. 424/251; 424/258; 424/266; 260/256.4 N; 260/287 R; 260/294.8 D; 260/294.8 F; 260/294.8 G; 260/294.9; 260/295.5 R; 260/295.5 A
[51] Int. Cl.² .................. C07D 213/55; A01N 9/22
[58] Field of Search............... 260/295.5 R, 294.8 F, 260/284.8 G, 295.5 A, 256.4 N; 424/260, 251

[56] References Cited
UNITED STATES PATENTS
| | | | |
|---|---|---|---|
| 3,867,393 | 2/1975 | Meyer et al.................. | 260/295.5 R |
| 3,883,540 | 5/1975 | Meyer et al.................. | 260/295.5 R |
| 3,917,622 | 11/1975 | Meyer et al.................. | 260/295.5 R |

*Primary Examiner*—Alan L. Rotman

[57] ABSTRACT

A new class of 1,4-dihydropyridines which are characterized by the presence of ester substitutes at positions 3 and 5 of the nucleus and by the presence of an alkoxyalkyl at position 2. The products exhibit coronary activity and have particular application as coronary dilators, anti-fibrillators, anti-hypertensives, and as muscular and vascular spasmolytics.

12 Claims, No Drawings

1,4-DIHYDROPYRIDINE ESTERS

CROSS-REFERENCE

This is a division of Ser. No. 485,300 filed July 2, 1974 now abandoned.

This invention relates to a new class of alkoxyalkyl-1,4-dihydropyridine ester products and to a method for their preparation. The products exhibit coronary dilator activity and, also, have utility as anti-hypertensive agents, anti-fibrillators, vascular spasmolytics and muscular spasmolytics.

It is known that 1,4-dihydropyridines possess interesting pharmacological activity as noted in F. Bossert and W. Vater, "Die Naturwissenschaften," 1971, 58th year of publication, issue 11, page 578, but the instant products are distinct therefrom and, by virtue of their pharmacological activity, represent a distinct advance in the art.

The products of this invention are alkoxyalkyl-1,4-dihydropyridine esters of the following formula:

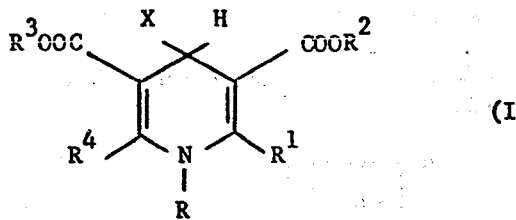

(I)

wherein
R is hydrogen, alkyl or alkenyl;
$R^1$ is alkoxyalkyl;
$R^2$ and $R^3$ are the same or different members selected from alkyl, alkenyl, alkynyl or cycloalkyl;
$R^4$ is hydrogen, alkyl, alkoxyalkyl, or carbalkoxyalkyl; and
X is aryl or substituted aryl wherein the nucleus is substituted by one, two or three of the same or different substituents selected from nitro, cyano, azido, alkyl, alkoxy, hydroxy, acyloxy, alkanoamido, amino, acylamino, monoalkylamino, dialkylamino, $S(O)_m$-alkyl in which $m$ is 0, 1 or 2, phenyl, trifluoromethyl or halo; or benzyl, styryl, cycloalkyl, cycloalkenyl, quinolyl, isoquinolyl, pyridyl, pyrimidyl, diphenyl, furyl, pyrryl or substituted pyrryl wherein the nucleus is substituted by one, two or three of the same or different substituents selected from alkyl, alkoxy, dialkylamino, nitro or halo; and the non-toxic pharmacologically acceptable salts thereof as, for example, the acid addition salts. These products (I) exhibit particularly good coronary dilator activity.

In the above formula (I), the difinitions of R, $R^1$, $R^2$, $R^3$, $R^4$ and X should be understood to include the following:

R includes straight and branched chain alkyl of 1 to 4, and preferably 1 to 3, carbon atoms such as methyl, ethyl, n-propyl, iso-propyl, n-butyl, iso-butyl or tertiary butyl; or straight or branched chain alkenyl of 2 to 4 carbon atoms, preferably 2 or 3 carbon atoms, such as ethenyl, propen-1-yl, propen-2-yl, or buten-3-yl;

$R^1$ and $R^4$ include alkoxyalkyl radicals of the formula —Y—O—Z, in which Y is straight or branched chain alkylene of 1 to 4 and, preferably 1 or 2 carbon atoms such as methylene, ethylene, n-propylene or iso-propylene, and Z is alkyl of 1 to 4 and, preferably, 1 or 2 carbon atoms, such as methyl, ethyl, n-propyl, iso-propyl, n-butyl, iso-butyl, secondary-butyl, or tertiary-butyl;

$R^2$ and $R^3$ include alkyl of 1 to 6 and preferably 1 to 4, carbon atoms such as methyl, n-propyl, iso-propyl, n-butyl, iso-butyl or tertiary-butyl, straight or branched chain alkenyl, preferably, alkenyl of 2 to 6, and most preferably 2 to 4, carbon atoms such as ethenyl, propen-1-yl, propen-2-yl, or buten-3-yl; straight or branched chain alkynyl of 2 to 6, and most preferably 2 to 4, carbon atoms such as ethynyl, propin-1-yl, propyn-2-yl, or butyn-2-yl; cycloalkyl includes monocyclic, bicyclic or tricyclic cycloalkyl, preferably of 3 to 10 carbon atoms and, most preferably, 3, 5 or 6 carbon atoms, such as cyclopropyl, cyclobutyl, cyclopentyl, cyclohexyl, cycloheptyl, bicyclo[2.2.1]heptyl, bicyclo[2.2.1]octyl or adamantyl.

Also included within the definition of $R^2$ and $R^3$ are the aforementioned alkyl, alkenyl, alkynyl, and cycloalkyl radicals wherein one or two hydrogen atoms may be substituted by one or more, but preferably one, hydroxy group. Preferred $R^2$ and $R^3$ substituents are those interrupted by one or two oxy moieties, preferably, alkyl, alkenyl, alkynyl and cycloalkyl moieties containing one oxy group within the chain.

$R^4$ in addition to alkoxyalkyl or carbalkoxyalkyl, can also be alkyl, preferably, of 1 to 6, and most preferably 1 to 4, carbon atoms such as methyl, ethyl, n-propyl, iso-propyl, n-butyl, iso-butyl, or tertiary-butyl;

X includes aryl, preferably, aryl of 6 to 10 carbon atoms in the nucleus and, most preferably phenyl or naphthyl.

Substituted aryl includes the aforementioned aryl moieties within the definition of X wherein the substituents are, preferably, one to three of the same or different substituents and, most preferably, one or two identical or different substituents. Illustrative of these substituents are: phenyl, alkyl, preferably, of 1 to 4, and most preferably 1 or 2, carbon atoms such as methyl, ethyl, n-propyl, iso-propyl, n-butyl, iso-butyl, or tertiary-butyl; alkoxy, preferably of 1 to 4, and most preferably 1 or 2, carbon atoms such as methoxy, ethoxy, n-propoxy, iso-propoxy, n-butoxy, iso-butoxy, or tertiary-butoxy; trifluoromethyl; hydroxy; halo such as fluoro, chloro, bromo or iodo, preferably chloro and bromo; cyano; nitro; azido; amino; monoalkylamino and dialkylamino, preferably of 1 to 4, and most preferably 1 or 2 carbon atoms per alkyl group such as methylamino, methylethylamino, n-propylamino, iso-propylamino or methyl-n-butylamino; alkanamido, preferably of 2 to 4, and most preferably 2 or 3, carbon atoms such as acetamido and propionamido; acyloxy, especially lower alkanoyloxy, preferably of 2 to 6, and most preferably 2 to 4, carbon atoms such as acetoxy and propionyloxy; and $S(O)_m$-alkyl, in which $m$ is an integer having a value of 0 to 2 and alkyl has 1 to 4, preferably 1 or 2, carbon atoms as, for example, methylthio, ethylthio, methylsulphinyl, ethylsulphinyl, methylsulphonyl and ethylsulphonyl.

The cycloalkyl radical within the definition of X is preferably a monocyclic, bicyclic or tricyclic cycloalkyl with preferably 3 to 10, and especially 3, 5 or 6, carbon atoms as, for example, cyclopropyl, cyclobutyl, cyclopentyl, cyclohexyl, cycloheptyl, bicyclo[2.2.1]heptyl, bicyclo[2.2.2]octyl and adamantyl.

The cycloalkenyl radical within the definition of X is preferably a monocyclic, bicyclic or tricyclic cycloalkenyl with preferably 5 to 10, and especially 5, 6 or 7, carbon atoms as, for example, cyclopentenyl, cyclohexenyl and cycloheptenyl.

The alkyl and alkoxy radicals which are present as substituents on the quinolyl, isoquinolyl, pyridyl, pyrimidyl, diphenyl, furyl and pyrryl nuclei X are, preferably, straight or branched chain alkyl and alkoxy with, preferably, 1 to 6, and most preferably 1 to 4, carbon atoms such as methyl, ethyl, n-propyl, iso-propyl, n-butyl, iso-butyl, tertiary-butyl, and methoxy, ethoxy, n-propoxy, iso-propoxy, n-butoxy, and tertiary-butoxy.

The halogen atoms which are present as substituents on the quinolyl, isoquinolyl, pyridyl, pyrimidyl, diphenyl, furyl and pyrryl nuclei X may be fluoro, chloro, bromo or iodo but, preferably, fluoro or chloro.

Dialkylamino radicals present as substituents on the quinolyl, isoquinolyl, pyridyl, pyrimidyl, diphenyl, furyl or pyrryl nuclei X preferably contain 1 to 4, and most preferably 1 or 2, carbon atoms per alkyl group. Typical examples of dialkyl-amino radicals are, for example, dimethylamino, diethylamino, di-n-propylamino, di-n-isopropylamino, di-n-butylamino, di-isobutylamino and di-tertiary-butylamino.

A preferred embodiment of this invention comprises those products of formula (I) wherein:
R is hydrogen;
$R^1$ is alkoxyalkyl wherein the alkyl moiety contains 1 or 2 carbon atoms and the alkoxy moiety contains 1, 2 or 3 carbon atoms;
$R^2$ and $R^3$ are the same or different alkyl of 1 to 4 carbon atoms, preferably methyl or ethyl;
$R^4$ is alkyl of 1 to 4 carbon atoms, preferably methyl or ethyl, alkoxyalkyl of 1 or 2 carbon atoms in the alkyl portion and 1 or 3 carbon atoms, but preferably 1 or 2 carbon atoms, in the alkoxy portion, carboxy, or —$CH_2$—COO alkyl wherein the alkyl contains 1 to 4 and, preferably 1 or 2, carbon atoms; and
X is phenyl or substituted phenyl wherein the benzene nucleus contains 1 or 2 substituents selected from alkoxy, preferably methoxy; alkylthio of 1 or 2 carbon atoms, preferably methylthio; cyano; nitro; hydroxy; trifluoromethyl; fluoro; chloro; iodo; alkanamido of 2 to 4 carbon atoms, preferably 2 or 3 carbon atoms; and alkylsulphonyl of 1 to 4 but, preferably, 1 or 2 carbon atoms.

The preferred salt of this invention are the non-toxic and physiologically well tolerated acid addition salts. Examples of inorganic and organic acids which form such salts with the compounds of formula (I) are, for example, the hydrohalic acids such as hydrochloric acid and hydrobromic acid but especially hydrochloric acid, phosphoric acid, sulphuric acid, nitric acid and monofunctional and bifunctional carboxylic and hydroxycarboxylic acids as, for example, acetic, maleic, succinic, fumaric, tartaric, citric, salicylic, sorbic, lactic and 1,5-naphthalenecarboxylic acids. The said salts are prepared by conventional means as, for example, by dissolving the base (I) in ether and adding the desired acid to the solution.

Surprisingly, the instant products (I) and the salts thereof exhibit a vry strong effect on blood vessels, especially a very strong coronary dilator effect.

This invention also relates to a method for the preparation of the new compounds described above, in which:

a. an enamine of the general formula:

is reacted with an ylidene derivative of the general formula:

or b. an enamine of the general formula:

is reacted with an ylidene derivative of the general formula:

or c. a β-ketocarboxylic acid ester of the general formula:

in reacted with an enamine of the general formula:

and an aldehyde of the general formula:

or d. a β-ketocarboxylic acid ester of the general formula:

is reacted with an enamine of the general formula:

and an aldehyde of the general formula:

or e. when $R^1$ is identical to $R^4$ and when $R^2$ is identical to $R_3$, two molar parts of a β-ketocarboxylic acid ester of the general formula:

are reacted with one molar part of an amine of the general formula:

  (III)

or a salt thereof, and with on part of an aldehyde of the general formula:

X—CHO  (IX);

wherein R, R¹, R², R³, R⁴ and X in the formulae III–IX are as defined above.

The new free alkoxyalkyl-1,4-dihydropyridine esters of the general formula I and their salts can be interconverted in any suitable manner, as for example, by employing conventional methods for interconverting free bases and the salts.

Throughout this specification the term "compounds according to the invention" includes both the alkoxyalkyl-1,4-dihydropyridine esters of general formula I and their salts.

The process of this invention designated above as (a) to (e) are illustrated by the following equations and will hereinafter be referred to as Process Variants (a) to (e).

A. If, for example, 3,4,5-trimethoxybenzylidene-acetoacetic acid methyl ester and β-methylamino-γ-isopropoxy-crotonic acid are used as starting materials, the course of the reaction for Process Variant (a) can be represented as follows:

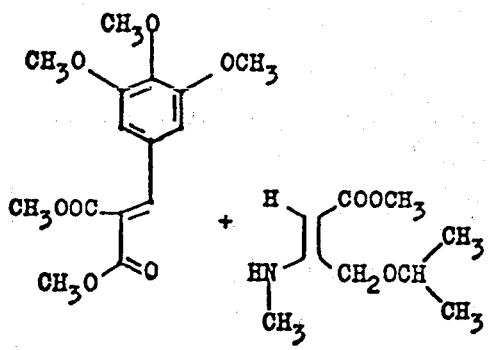

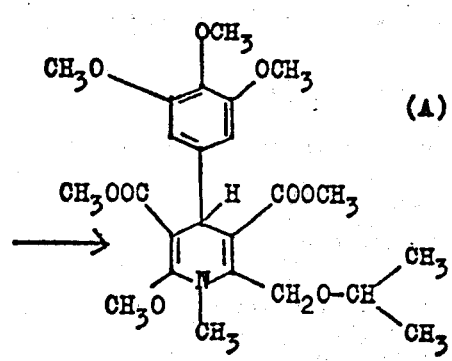

(A)

The β-methylamino-γ-isopropoxy-crotonic acid used as starting material can be prepared by reacting γ-isopropoxyacetoacetic acid methyl ester and methylamine.

B. If, for example, 3-chlorobenzylidene-γ-methoxy-acetoacetic acid ethyl ester and β-imino-glutaric acid ethyl ester are usued as starting materials, the course of the reaction for Process Variant (b) can be represented as follows:

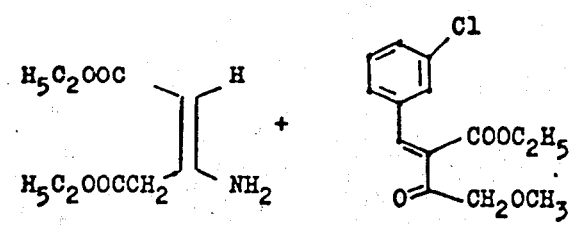

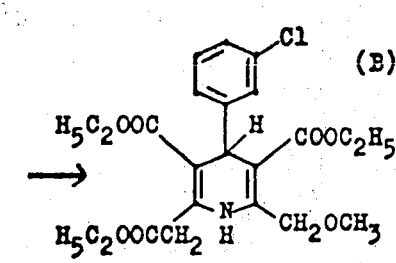

(B)

The β-iminoglutaric acid ethyl ester used as starting material can be prepared from acetone dicarboxylic acid diethyl ester and ammonia.

C. If, for example, 3-ethyl-sulphonylbenzaldehyde, β-amino-γ-methoxycrotonic acid propyl ester and propionylacetic acid ethyl ester are used as starting materials, the course of the reaction for Process Variant (c) can be represented as follows:

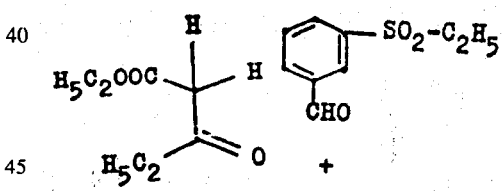

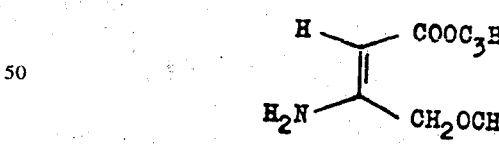

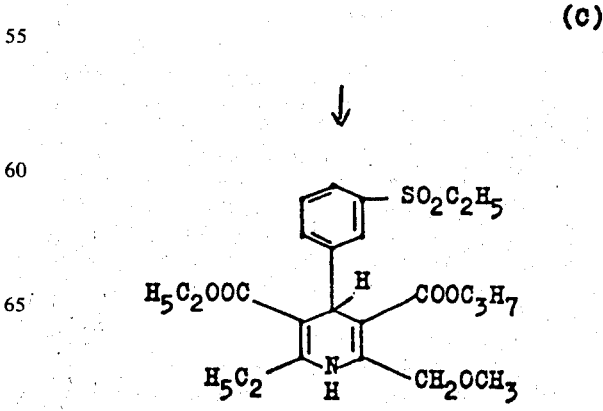

(C)

D. If, for example, pyridine-2-aldehyde, γ-methoxyacetoacetic acid methyl ester and β-amino-γ-ethoxy-crotonic acid ethyl ester are used as starting materials, the course of the reaction for Process Variant (d) can be represented as follows:

E. If, for example, 3-nitro-benzaldehyde, 2 parts of γ-methoxyacetoacetic acid diethyl ester and ammonia are used as starting materials, the course of the reaction for Process Variant (e) can be represented as follows:

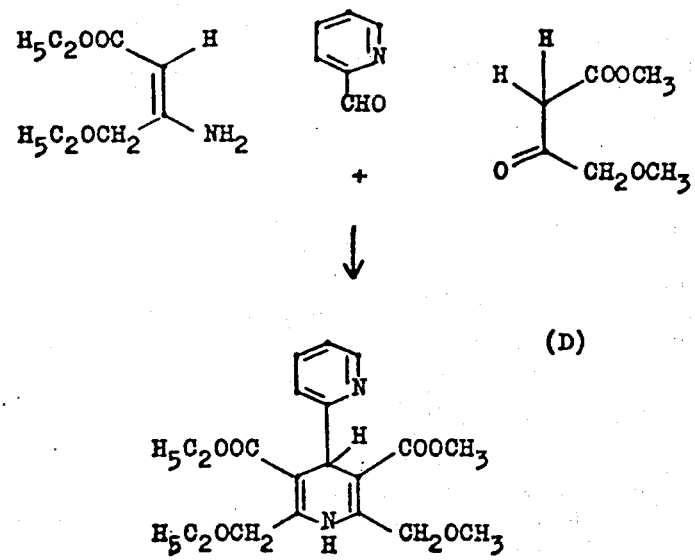

(D)

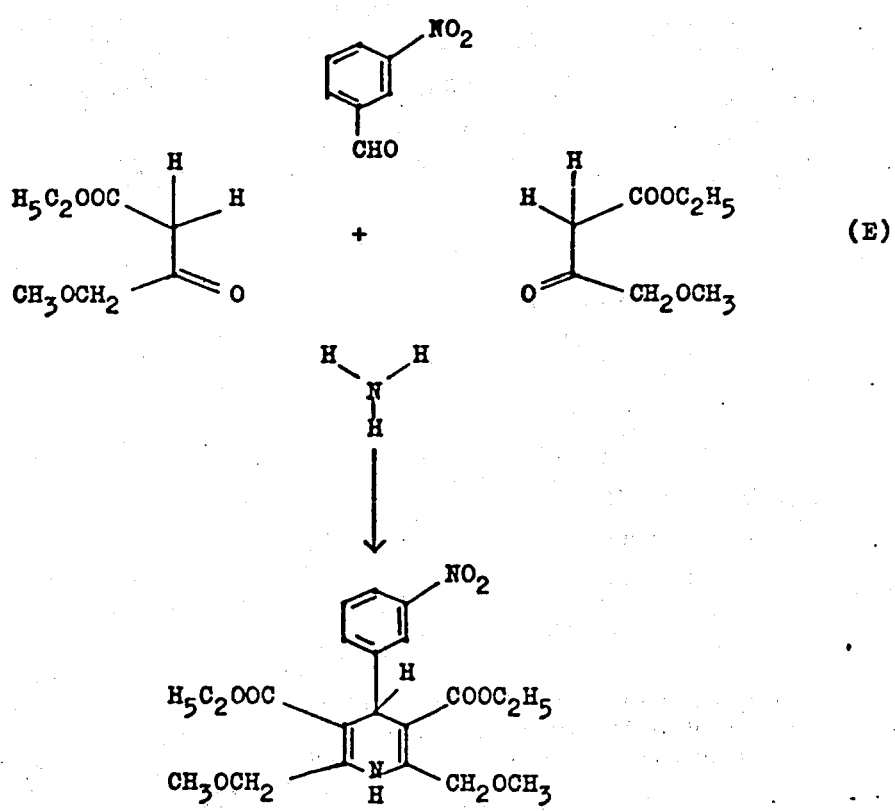

(E)

Provess Variant (a) according to this invention preferably comprises also the prior step of producing the enamine of the general formula (IV) by reacting a β-ketocarboxylic acid ester of the general formula:

with an amine of the general formula:

wherein the R, R¹ and R² in formulae II and III are as defined above.

Similarly, Process Variant (b) according to this invention preferably comprises also the prior step of producing the enamine of general formula (VII) by reacting a β-ketocarboxylic acid ester of the general formula:

with an amine of the general formula:

wherein in formulae (VI) and (III) R, R³ and R⁴ are as defined above.

The enamines (IV) and (VII) thus produced may be isolated and purified before reaction according to Process Variants (a) and (b) with the ylidene derivatives of general formulae (V) and (VIII) respectively, or may be reacted with them in situ without intermediate isolation.

The β-ketocarboxylic acid esters of the general formula (II) which can be used as starting materials in Process Variants (a) and (b) according to the invention are known or can be prepared according to known processes, as shown by B. Johnson and H. Chesnoff, J.A.C.S. 36, 1744 (1914).

As Examples of the esters of general formula II there may be mentioned:
γ-methoxyacetoacetic acid methyl ester,
γ-methoxyacetoacetic acid ethyl ester,
γ-methoxyacetoacetic acid propyl ester,
γ-methoxyacetoacetic acid isopropyl ester,
γ-methoxyacetoacetic acid butyl ester,
γ-ethoxyacetoacetic acid methyl ester,
γ-ethoxyacetoacetic acid ethyl ester,
γ-ethoxyacetoacetic acid propyl ester,
γ-propoxyacetoacetic acid ethyl ester,
γ-propoxyacetoacetic acid isopropyl ester,
γ-propoxyacetoacetic acid t.-butyl ester,
γ-isopropoxyacetoacetic acid methyl ester,
γ-isopropoxyacetoacetic acid butyl ester,
γ-butoxyacetoacetic acid ethyl ester,
γ-butoxyactoacetic acid isobutyl ester,
γ-isobutoxyacetoacetic acid propyl ester,
γ-methoxypropionylacetic acid methyl ester,
γ-methoxypropionylacetic acid ethyl ester,
γ-propoxypropionylacetic acid propyl ester,
δ-ethoxypropionylacetic acid ethyl ester and
δ-methoxy-γ-ethylpropionylacetic acid ethyl ester.

The amines of the general formula III which can be used as starting materials in Process Variants (a), (b) and (e) according to the invention are as a class already known. Examples of these amines are the following:
ammonia,
methylamine,
ethylamine,
propylamine,
butylamine,
isopropylamine,
isobutylamine, and
allylamine.

The enamine-β-keto-carbonyl compounds of the general formula II which can be used as starting materials in Process Variants (a) and (c) according to the invention can be prepared according to generally known methods from the corresponding β-diketo compounds, as shown by A. C. Cope, J.A.C.S. 67, 1017 (1945). Examples of these enamines are the following:
γ-methoxy-β-aminocrotonic acid methyl ester,
γ-methoxy-β-aminocrotonic acid ethyl ester,
γ-ethoxy-β-aminocrotonic acid propyl ester,
γ-isopropoxy-β-methylaminocrotonic acid ethyl ester, and
γ-butoxy-γ-methyl-β-aminocrotonic acid ethyl ester.

The ylidene-β-ketocarboxylic acid esters of the general formula V which can be used as starting materials in Process Variant (a) according to the invention are either known or can be prepared according to methods which are generally known, as shown by Org. Reactions XI, 204 et seq. (1967). Examples of typical ylidene derivatives are the following ylidene-β-ketocarboxylic acid esters:
benzylidene-γ-methoxyacetoacetic acid ethyl ester,
2'-nitrobenzylidene-γ-methoxyacetoacetic acid ethyl ester,
3'-methoxybenzylidene-γ-ethoxyacetoacetic acid methyl ester,
3',4'-dimethoxybenzylidene-γ-propoxyacetoacetic acid propyl ester,
2'-trifluoromethylbenzylidene-γ-methoxyacetoacetic acid ethyl ester,
2-chlorobenzylidene-γ-ethoxyacetoacetic acid propyl ester,
3-mercaptobenzylidene-γ-butoxyacetoacetic acid ethyl ester,
benzylideneacetoacetic acid methyl ester,
2'-nitrobenzylideneacetoacetic acid methyl ester,
3'-nitrobenzylideneacetoacetic acid propargyl ester,
3'-nitrobenzylideneacetoacetic acid allyl ester,
3'-nitrobenzylideneacetoacetic acid γ-ethoxyethyl ester,
4'-nitrobenzylideneacetoacetic acid isopropyl ester,
3'-nitro-6'-chlorobenzylideneacetoacetic acid methyl ester,
2'-cyanobenzylidenepropionylacetic acid ethyl ester,
3'-cyanobenzylideneacetoacetic acid methyl ester,
3'-nitro-4'-chlorobenzylideneacetoacetic acid t.-butyl ester,
2'-nitro-4'-methoxybenzylideneacetoacetic acid methyl ester,
2'-cyano-4'-methylbenzylideneacetoacetic acid ethyl ester,
2'-azidobenzylideneacetoacetic acid ethyl ester,
2'-methylmercaptobenzylideneacetoacetic acid isopropyl ester, 2'-sulphinylmethylbenzylideneacetoacetic acid ethyl ester,
2-sulphonylmethylacetoacetic acid ethyl ester,
2'-nitrobenzylideneoxalacetic acid diethyl ester,
2',4'-dioxymethylenebenzylideneoxalacetic acid dimethyl ester,
3'-ethoxybenzylidene-β-ketoglutaric acid diethyl ester,
(2'-ethoxy-1'-naphhylidene)-acetoacetic acid methyl ester,
(1'-isoquinolyl)-methylideneacetoacetic acid methyl ester,
α-pyridylmethylideneacetoacetic acid methyl ester,
α-pyridylmethylideneacetoacetic acid allyl ester,
α-pyridylmethylideneacetoacetic acid cyclohexyl ester,
β-pyridylmethylideneacetoacetic acid β-methoxyethyl ester,
6-methyl-α-pyridylmethylideneacetoacetic acid ethyl ester,
4',6'-dimethoxy-(5'-pyrimidyl)-methylideneacetoacetic acid ethyl ester,
(2'-thenyl)-methylideneacetoacetic acid ethyl ester,
(2'-furyl)-methylideneacetoacetic acid allyl ester,
(2'-pyrryl)-methylideneacetoacetic acid methyl ester,
α-pyridylmethylidenepropionylacetic acid methyl ester,
2'-, 3'- and 4'-methoxybenzylideneacetoacetic acid ethyl esters,
2'-methoxybenzylideneacetoacetic acid propargyl ester,
2'-isopropoxybenzylideneacetoacetic acid ethyl ester,
3'-butoxybenzylideneacetoacetic acid methyl ester,
3',4',5'-trimethoxybenzylideneacetoacetic acid allyl ester,
2'-methylbenzylidenepropionylacetic acid methyl ester,
2'-methylbenzylideneacetoacetic acid β-propoxyethyl ester,
3', 4'-dimethoxy-5'-bromobenzylideneacetoacetic acid ethyl ester,
2'-, 3'- and 4'-chloro-/bromo-/fluoro-/iodo-benzylideneacetoacetic acid ethyl esters,
3'-chlorobenzylidenepropionylacetic acid ethyl ester,
2'-, 3'- and 4'-trifluoromethylbenzylideneacetoacetic acid propyl esters,
2'-carbethoxybenzylideneacetoacetic acid ethyl ester, and
4-carboxyisopropylbenzylideneacetoacetic acid isopropyl ester.

The β-ketocarboxylic acid esters of the general formula VI and the enamino-β-ketocarboxylic acid esters of the general formula VII, which can be used as starting materials in Process Variants (b), (c), (d) and (e) according to the invention, are known or can be prepared according to methods which are generally known (B. Johnson and H. Chesnoff, J.A.C.S. 36, 1744 (1914); Pohl and Schmidt, U.S. Pat. 2,351,366; A. C. Cope, J.A.C.S. 67, 1067 (1945)). Examples of these esters and enamines are the following β-dicarbonyl compounds:

γ-methoxyacetoacetic acid methyl ester,
γ-methoxyacetoacetic acid ethyl ester,
γ-methoxyacetoacetic acid propyl ester,
γ-methoxyacetoacetic acid isopropyl ester,
γ-methoxyacetoacetic acid butyl ester,
γ-ethoxyacetoacetic acid methyl ester,
γ-ethoxyacetoacetic acid ethyl ester,
γ-ethoxyacetoacetic acid propyl ester,
γ-propoxyacetoacetic acid ethyl ester,
γ-propoxyacetoacetic acid isopropyl ester,
γ-propoxyacetoacetic acid t.-butyl ester,
γ-isopropoxyacetoacetic acid methyl ester,
γ-isopropoxyacetoacetic acid butyl ester,
γ-butoxyacetoacetic acid ethyl ester,
γ-butoxyacetoacetic acid isobutyl ester,
γ-isobutoxyacetoacetic acid propyl ester,
γ-methoxypropionylacetic acid methyl ester,
γ-methoxypropionylacetic acid ethyl ester,
γ-propoxypropionylacetic acid propyl ester,
δ-ethoxypropionylacetic acid ethyl ester,
δ-methoxy-γ-ethylpropionylacetic acid ethyl ester,
3,5-formylacetic acid ethyl ester,
formylacetic acid butyl ester,
acetoacetic acid methyl ester,
acetoacetic acid ethyl ester,
acetoacetic acid methyl ester,
acetoacetic acid isopropyl ester,
acetoacetic acid butyl ester,
acetoacetic acid t.-butyl ester,
acetoacetic acid α- and β-hydroxyethyl esters,
acetoacetic acid α- and β-methoxyethyl esters,
acetoacetic acid α- and β-ethoxyethyl esters,
acetoacetic acid α- and β-n.-propoxyethyl esters,
acetoacetic acid allyl ester,
acetoacetic acid propargyl ester,
propionylacetic acid ethyl ester,
butyrylacetic acid ethyl ester,
isobutyrylacetic acid ethyl ester,
oxalacetic acid dimethyl ester,
oxalacetic acid diethyl ester,
oxalacetic acid isopropyl ester,
acetonedicarboxylic acid dimethyl ester,
acetonedicarboxylic acid diethyl ester,
acetonedicarboxylic acid dibutyl ester, and
β-ketoadipic acid diethyl ester.
Enaminecarboxylic acid esters:
γ-methoxy-β-aminocrotonic acid methyl ester,
γ-methoxy-β-aminocrotonic acid ethyl ester,
γ-ethoxy-β-aminocrotonic acid propyl ester,
γ-isopropoxy-β-methylaminocrotonic acid ethyl ester,
γ-butoxy-γ-methyl-β-aminocrotonic acid ethyl ester,
β-aminocrotonic acid methyl ester,
β-aminocrotonic acid ethyl ester,
β-aminocrotonic acid isopropyl ester,
β-aminocrotonic acid butyl ester,
β-aminocrotonic acid α- and β-methoxyethyl esters,
β-aminocrotonic acid β-ethoxyethyl ester,
β-aminocrotonic acid β-propoxyethyl ester,
β-aminocrotonic acid t.-butyl ester,
β-aminocrotonic acid cyclohexyl ester,
β-amino-β-ethylacrylic acid ethyl ester,
iminosuccinic acid dimethyl ester,
iminosuccinic acid diethyl ester,
iminosuccinic acid dipropyl ester,
iminosuccinic acid dibutyl ester,
β-iminoglutaric acid dimethyl ester,
β-iminoglutaric acid diethyl ester,
β-iminoadipic acid dimethyl ester,
βiminoadipic acid diisopropyl ester,
β-methylaminocrotonic acid methyl ester,
β-ethylaminocrotonic acid ethyl ester, and β-methyliminoglutaric acid diethyl ester.

The ylidene-β-ketocarboxylic acid esters of the general formula VIII which can be used in Process Variant (b) according to the invention are not yet known. They can however, as mentioned already for compounds of the general formula V, be prepared according to methods which are generallly known. Examples of these ylidene derivatives are the following ylidene-β-ketocarboxylic acid esters:

benzylidene-γ-ethoxyacetoacetic acid methyl ester,
2'-nitrobenzylidene-γ-propoxyacetoacetic acid methyl ester,
3'-nitrobenzylidene-γ-methoxyacetoacetic acid methyl ester,
3'-nitrobenzylideneacetoacetic acid propyl ester,
4'-nitrobenzylidene-γ-methoxyacetoacetic acid isopropyl ester,
3'-nitro-6'-chlorobenzylidene-γ-isopropoxyacetoacetic acid methyl ester,
2'-cyanobenzylidene-γ-n.-butoxyacetoacetic acid methyl ester,
2'-cyanobenzylidene-δ-ethoxypropionylacetic acid ethyl ester,
2'-nitro-4'-methoxybenzylidene-γ-propoxyacetoacetic acid methyl ester,
2'-azidobenzylidene-γ-methoxyacetoacetic acid ethyl ester,
2'-methylmercaptobenzylidene-γ-ethoxyacetoacetic acid methyl ester,
3'-methylmercaptobenzylidene-γ-methoxyacetoacetic acid isopropyl ester,
2'-sulphinylmethylbenzylideneacetoacetic acid ethyl ester,
2'-sulphonylmethyl-γ-methoxyacetoacetic acid ethyl ester,
(2'-ethoxy-1'-naphthylidene)-γ-methoxyacetoacetic acid methyl ester,
(1'-isoqinolyl)-methylidene-γ-ethoxyacetoacetic acid methyl ester,
α-pyridylmethylidene-γ-propoxyacetoacetic acid ethyl ester,
4',6'-dimethoxy-(5'-pyrimidyl)-methylidene-γ-methoxyacetoacetic acid ethyl ester,
(2'-thenyl)-γ-methoxymethylideneacetoacetic acid ethyl ester,
(2'-furyl)-γ-ethoxymethylideneacetoacetic acid butyl ester,
2'-, 3'- and 4'-methoxybenzylidene-γ-methoxyacetoacetic acid ethyl esters,
2'-isopropoxybenzylidene-γ-isopropoxyacetoacetic acid ethyl ester,
3'-butoxybenzylidene-γ-methoxyacetoacetic acid methyl ester,
3', 4', 5'-trimethoxybenzylidene-γ-propoxyacetoacetic acid propyl ester,
2'-methylbenzylidene-δ-methoxypropionylacetic acid methyl ester,
2'-, 3'- and 4'-trifluoromethylbenzylidene-γ-methoxyacetoacetic acid propyl esters,
2'-trifluoromethylbenzylidene-γ-methoxyacetoacetic acid isopropyl ester,
3'-trifluoromethylbenzylidene-γ-ethoxyacetoacetic acid methyl ester,
2'-carbethoxybenzylidene-γ-methoxyacetoacetic acid ethyl ester,
3'-carboxymethylbenzylidene-γ-ethoxyacetoacetic acid methyl ester, and
4-carboxyisopropylbenzylidene-γ-propoxyacetoacetic acid isopropyl ester.

The aldehydes of the general formula IX which are used in Process Variants (c), (d) and (e) according to the invention are already known of can be prepared by known methods (E. Mosettig, Org. Reactions, VIII, 218 et seq. (1954)). Examples of these aldehydes are the following:

benzaldehyde,
2-, 3- and 4-methoxybenzaldehydes,
2-isopropoxybenzaldehyde,
3-butoxybenzaldehyde,
3,4-dioxymethylenebenzaldehyde,
3,4,5-trimethoxybenzaldehyde,
2-, 3- and 4-chloro-/bromo-/iodo-/fluoro/benzaldehydes,
2,4- and 2,6-dichlorobenzaldehyde,
2,4-dimethylbenzaldehyde,
3,5-diisopropyl-4-methoxybenzaldehyde,
2-, 3- and 4-nitrobenzaldehyde,
2,4- and 2,6-dinitrobenzaldehyde,
2-nitro-6-bromobenzaldehyde,
2-nitro-3-methoxy-6-chlorobenzaldehyde,
2-nitro-4-chlorobenzaldehyde,
2-nitro-4-methoxybenzaldehyde,
2-, 3- and 4-trifluoromethylbenzaldehyde,
2-, 3- and 4-dimethylaminobenzaldehydes,
4-dibutylaminobenzaldehyde,
4-acetaminobenzaldehyde,
2-, 3- and 4-cyanobenzaldehydes,
2-nitro-4-cyanobenzaldehyde,
3-chloro-4-cyanobenzaldehyde,
2-, 3- and 4-methylmercaptobenzaldehydes,
2-methylmercapto-5-nitrobenzaldehyde,
2-butylmercaptobenzaldehyde,
2-, 3- and 4-methylsulphinylbenzaldehydes,
2-, 3- and 4-methylsulphonylbenzaldehydes,
benzaldehyde-2-carboxylic acid ethyl ester,
benzaldehyde-3-carboxylic acid isopropyl ester,
benzaldehyde-4-carboxylic acid butyl ester,
3-nitrobenzaldehyde-4-carboxylic acid ethyl ester,
cinnamaldehyde,
hydrocinnamaldehyde,
formylcyclohexane,
1-formylcyclohexane-3,
1-formylcyclohexine-1,3,
1-formylcyclopentene-3,
α, β- and γ-pyridinaldehydes,
6-methylpyridin-2-aldehyde,
furan-2-aldehyde,
thiophen-2-aldehyde,
pyrrole-2-aldehyde,
N-methylpyrrole-2-aldehyde,
2-, 3- and 4-azidobenzaldehydes,
pyrimidin-4-aldehyde,
5-nitro-6-methylpyridin-2-aldehyde,
1- and 2-naphthaldehydes,
5-bromo-1-naphthaldehyde,
quinoline-2-aldehyde,
7-methoxyquinoline-4-aldehyde, and
isoquinoline-1-aldehyde.

As diluents in Process Variants (a) to (e) water and/or any inert organic solvent can be used. Preferred diluents include alcohols, preferably, alkanols of 1 to 4 carbon atoms, such as ethnoal, methanol and isopropanol, ethers, preferably, straight chain di-alkyl ethers of 3 to 5 carbon atoms, such as diethyl ether or cyclic ethers such as tetrahydrofuran or dioxane, aliphatic carboxylic acids, preferably those of 2 to 5 carbon atoms such as acetic acid and propionic acid, di-alkyl-formamides, preferably, those of 1 or 2 carbon atoms per alkyl group such as dimethylformamide, alkyl nitriles, preferably, those of 2 to 4 carbon atoms such as acetonitrile, dimethylsulphoxide, and liquid heterocyclic bases such a pyridine or mixtures of two or more of said diluents and mixtures of one or more of said diluents with water.

In Process Variants (a) to (e) the reaction temperatures can be varied over a substantial range. Generally, the reaction is carried out between 20° and 150 C, preferably between 50° and 100°C and, most preferably, at the boiling of the diluent employed.

The reaction can be carried out under atmospheric pressure but also under elevated pressure. In general, atmospheric pressure is employed.

In carrying out the Process Variants (a) to (e) according to this invention, the starting compounds are preferably employed in approximately equimolar amounts. When an amine (III) is used, or its salt, it is preferred to use an excess of 1 to 2 mols. The molar ratios can be varied over a substantial range without having an adverse influence on the function.

In addition to the new compounds described in the following Examples, the following may be mentioned as products of this invention:

1-methyl-2,6-dimethoxymethyl-4-(3', 5'-dihydroxy-4'-iodophenyl)-1,4-dihydropyridine-3,5-dicarboxylic acid dipropyl ester, 2-propyl-6-propoxymethyl-4-(2'-methylsulphenyl-phenyl)-1,4-dihydropyridine-3-carboxylic acid propyl ester-5-carboxylic acid isopropyl ester, 1-isopropyl-2,6-dimethoxymethyl-4-(3-azido-phenyl)-1,4-dihydropyridine-3,5-dicarboxylic acid diethyl ester, 2,6-dimethoxymethyl-4-(3-carboxyphenyl)-1,4-dihydropyridine-3,5-dicarboxylic acid dibutyl ester, 1-benzyl-2,6-dipropoxymethyl-4-(3'-quinolyl)-1,4-dihydropyridine-3-carboxylic acid methyl ester-5-carboxylic acid propyl ester, 1,2-dibutyl-6-butoxyethyl-4-($\alpha$-pyridyl)-1,4-dihydropyridine-3,5-dicarboxylic acid dibutyl ester, 2,6-diethoxyethyl-4-(isoquinolyl)-1,4-dihydropyridine-3-carboxylic acid ethyl ester 5-carboxylic acid isobutyl ester, 2,6-dimethoxymethyl-4-(5'-[4,6-dimethoxy]-pyrimidyl)-1,4-dihydropyridine-3,5-dicarboxylic acid diethyl ester, 1-ethyl-2-methoxyethyl-6-propyl-4-(2'-[5'-nitrofuryl])-1,4-dihydropyridine-3-carboxylic acid-$\beta$-(ethoxyethyl ester), 2,6-dibutoxymethyl-4-(2'-N-propylpyrryl)-1,4-dihydropyridine-3,5-dicarboxylic acid dimethyl ester, 2,6-dimethoxymethyl-4-(3'-nitro-4'-hydroxypheny)-1,4-dihydropyridine-3-carboxylic acid methyl-5-carboxylic acid isopropyl ester, and 2-methoxymethyl-6-isopropocyethyl-4-(2'- 4'-bromothienyl)-1,4-dihydropyridine-3-carboxylic acid methyl ester-5-carboxylic acid propyl ester.

The pharmaceutical compositions of the present invention contain a major or minor amount e.g. 99.5 to 0.1%, preferably 95 to 0.5% of at least one compound (I) as above defined in combination with a pharmaceutically acceptable non-toxic, inert diluent or carrier, the carrier comprising one or more solid, semi-solid or liquid diluent, or liquified gaseous diluent filler and fomulation adjuvant which is non-toxic, inert and and pharmaceutically acceptable. The liquid should be other than a solvent having a molecular weight of less than 200 except when a surface active agent is also present.

The invention further provides a pharmaceutical composition containing as active ingredient a compound of the invention in the form of a sterile or isotonic aqueous solution. The instant compositions are preferably in dosage unit form; i.e., in physically discrete units containing a predetermined amount of the drug corresponding to a fraction of multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Also in addition to a compound of the invention, the pharmaceutical compositions and medicaments according to the invention can also contain other pharmaceutically active compounds. They may also contain one or more of the compounds (I) of this invention.

The pharmaceutical compositions of this invention may, for example, take the form of ointments, gels, pastes, creams, sprays (including aerosols), lotions, suspensions, solutions and emulsions of the active ingredient in aqueous or non-aqueous diluents, syrups, granules or powders.

The diluents to be used in pharmaceutical compositions (e.g. granulates) adapted to be formed into tablets, dragees, capsules and pills include the following:

(a) fillers and extenders, e.g. starch, sugars, manitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The active ingredient (I) can also e made up in microencapsulated form together with one or several of the abovementioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder to mixtures of these substances. Aerosol sprays can, for example, contain the usual propellants, e.g. chlorofluorohydrocarbons.

The pharmaceutical compositions which are solutions and emulsions can, for example, contain the customary diluents such as solvents, dissolving agents and emulsifiers extending those solvents having a molecular weight below 200 except in the presence of a surface-active agent; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The production of the above-mentioned pharmaceutical compositions and medicaments is carried out by conventional means as, for example, by mixing the active ingredient with the diluent to form a pharmaceutical composition as, for example, a granulate and then forming the composition into the medicament such as a tablet.

This invention further provides a method of combatting, including the prevention, relief and cure of, the abovementioned diseases in human and non-human animals, which comprises administering to the animals a compound of the invention alone or in admixture with a diluent or in the form of a medicament according to this invention.

It is envisaged that these active compounds will be administered perorally, parenterally as, for example, intramuscularly, intraperitoneally or intravenously, or rectally, preferably perorally or parenterally, especially perlingually or intravenously. Preferred pharmaceutical compositions and medicaments are therefore those adapted for peroral or parenteral, especially perlingual or intravenous administration, such as tablets, capsules (especially instant oral-release capsules) and ampoules of injectable solution. Administration in the method of the invention is preferably peroral or parenteral, especially perlingual or intravenous.

In general it has proved advantageous to administer the active compound(s), in the case of parenteral (in-travenous) administration, in amounts of about 0.005 to about 10, preferably of 0.02 to 5, mg/kg of body weight per 24 hours, and, in the case of oral administration, in amounts of about 0.1 to about 50, preferably 1 to 30, mg/kg of body weight per 24 hours, optionally in the form of several individual administrations, in order to achieve the desired results. An individual administration contains the active compound or the active compounds preferably in amounts of about 0.1 to about 10, especially 0.2 to 5, mg/kg of body weight. However, it can be necessary to deviate from the dosages mentioned and in particular to do so as a function of the nature and body weight of the subject to be treated, the nature and the severity of the illness, the nature of the preparation and of the administration of the medicine and the point in time or interval at which the administration is effected. Thus it may suffice, in some cases, to manage with less than the abovementioned amount of active compound whilst in other cases the abovementioned amount of active compound must be exceeded. The particularly required optimum dosage and type of administration of the active compounds can be laid down easily by any expert on the basis of his expert knowledge.

The following Examples illustrate the production of compounds according to the invention by the process according to the invention.

EXAMPLE 1

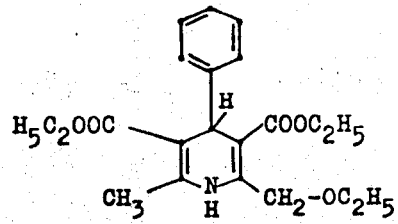

After heating a solution of 10.6 g of benzaldehyde, 17.4 g of γ-ethoxyacetoacetic acid ethyl ester and 13 g of β-aminocrotonic acid ethyl ester in 80 ml of ethanol for several hours, 2-ethoxymethyl-6-methyl-4-phenyl-1,4-dihydropyridine-3,5-dicarboxylic acid diethyl ester is obtained, in a yield of 65% of theory, in the form of yellow crystals of melting point 112°C.

EXAMPLE 2

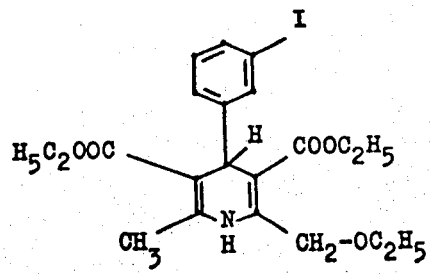

A solution of 5.8 g of 3-iodobenzaldehyde, 4.4 g of γ-ethoxyacetoacetic acid ethyl ester and 3.3 g of β-aminocrotonic acid ethyl ester in 30 ml of ethanol is heated to the boil overnight and is then cooled. After cooling, 2-ethoxymethyl-6-methyl-4-(3'-iodophenyl)-1,4-dihydropyridine-3,5-dicarboxylic acid diethyl ester

EXAMPLE 3

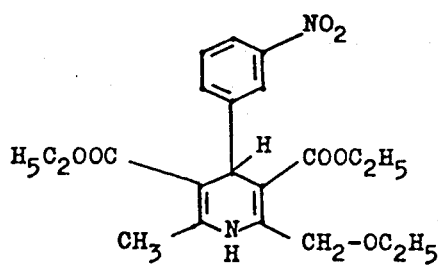

15 g of 3-nitrobenzaldehyde, 18 g of γ-ethoxyacetoacetic acid ethyl ester and 13 g of β-aminocrotonic acid ethyl ester are heated in 60 ml of ethanol for about 5 hours, the mixture is cooled and the product is filtered off and rinsed with cold ethanol. 2-Ethoxymethyl-6-methyl-4-(3'-nitrophenyl)-1,4-dihydropyridine-3,5-dicarboxylic acid diethyl ester is obtained, in the form of light yellow crystals of melting point 120°–122°C, in a yield of 70% of theory.

EXAMPLE 4

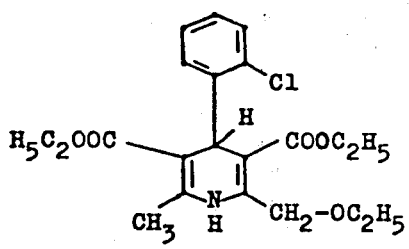

After heating a solution of 14 g of 2-chlorobenzaldehyde, 17.4 g of γ-ethoxyacetoacetic acid ethyl ester and 13 g of β-aminocrotonic acid ethyl ester in 80 ml of ethanol under reflux for several hours, 2-ethoxymethyl-6-methyl-4-(2'-chlorophenyl)-1,4-dihydropyridine-3,5-dicarboxylic acid diethyl ester is obtained, after cooling, in the form of light yellow crystals of melting point 115°C, in a yield of 55% of theory.

EXAMPLE 5

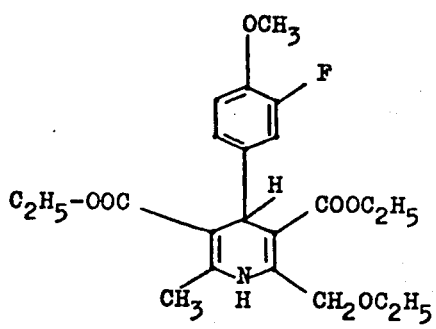

15.4 g of 3-fluoro-4-methoxybenzaldehyde, 17.4 g of γ-ethoxyacetoacetic acid ethyl ester and 13 g of β-aminocrotonic acid ethyl ester in 80 ml of ethanol are heated to the boil overnight, the mixture is cooled, and after filtration and rinsing with cold ethanol, 2-ethoxymethyl-6-methyl-4-(3'-fluoro-4'-methoxyphenyl)-1,4-dihydropyridine-3,5-dicarboxylic acid diethyl ester is obtained in 35% yield of theory, in the form of white crystals of melting point 120°C.

EXAMPLE 6

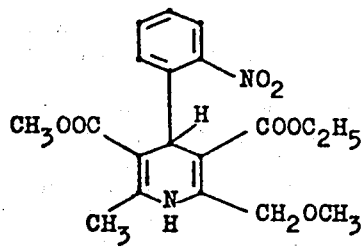

After heating a solution of 6.2 g of 2-nitrobenzaldehyde, 6.6 g of γ-methoxyacetoacetic acid ethyl ester and 4.8 g of β-aminocrotonic acid methyl ester in ethanol under reflux for 6 to 8 hours, the mixture is cooled and the product is filtered off and rinsed with a little cold ethanol. 2-Methoxy-methyl-6-methyl-4-(2'-nitrophenyl)-1,4-dihydropyridine-3,5-carboxylic acid ethyl ester-3,5-dicarboxylic acid methyl ester is obtained in the form of light yellow crystals of melting point 143°–145°C.

Yield: 45% of theory.

EXAMPLE 7

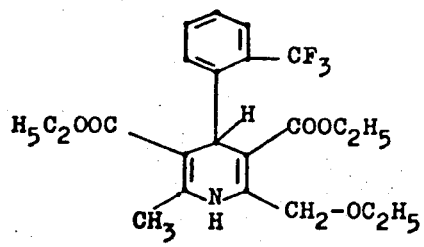

7.4 g of 2-trifluoromethylbenzaldehyde, 17.4 g of γ-ethoxyacetoacetic acid ethyl ester and 13 g of β-aminocrotonic acid ethyl ester in 80 ml of ethanol are heated under reflux overnight, the mixture is cooled and 2-ethoxymethyl-6-methyl-4-(2'-trifluoromethylphenyl)-1,4-dihydropyridine-3,5-dicarboxylic acid diethyl ester is obtained in the form of white-yellow crystals of melting point 112°C, in a yield of 55% of theory.

EXAMPLE 8

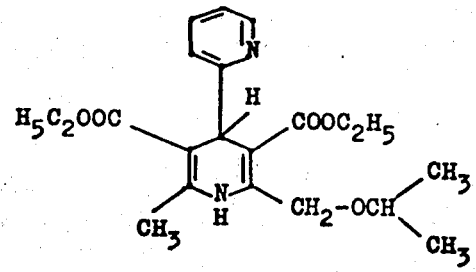

A solution of 10.4 ml of pyridin-2-aldehyde, 19 g of γ-isopropoxyacetoacetic acid ethyl ester (boiling point 106°–108°C/12 mm) and 13 g of β-aminocrotonic acid ethyl ester in 60 ml of ethanol is kept at the boil for 6–8 hours and then cooled, and 2-isopropoxymethyl-6-methyl-4-α-pyridyl-1,4-dihydropyridine-3,5-dicarboxylic acid ethyl ester is obtained, in the form of light yellow crystals of melting point 184°C, in a yield of 35% of theory.

EXAMPLE 9

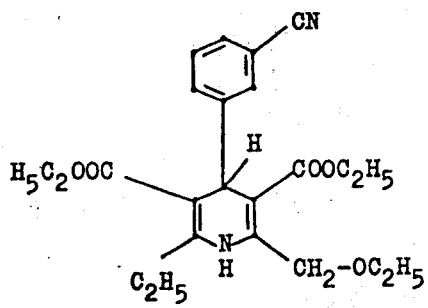

6.5 g of 3-cyanobenzaldehyde, 8.7 g of γ-ethoxyaceto-acetic acid ethyl ester and 7.2 g of β-amino-β-ethylacrylic acid ethyl ester in 80 ml of ethanol are heated overnight under reflux, the mixture is cooled, and after filtration, and washing with cold ethanol, 2-ethoxymethyl-6-ethyl-4-(3'-cyanophenyl)-1,4-dihydropyridine-3,5-dicarboxylic acid diethyl ester is obtained in the form of light yellow crystals of melting point 125°C, in a yield of 42% of theory.

EXAMPLE 10

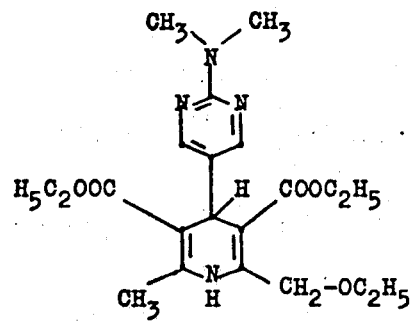

7.5 g of 2-dimethylaminopyrimidin-5-aldehyde, 8.7 g of γ-ethoxyacetoacetic acid ethyl ester and 6.5 g of β-aminocrotonic acid ethyl ester in 40 ml of ethanol are heated to the boil overnight and after cooling and filtration 2-ethoxymethyl-6-methyl-4-(2'-dimethylaminopyrimidyl)-1,4-dihydropyridine-3,5-dicarboxylic acid diethyl ester is obtained in the form of light beige crystals of melting point 124°C, in a yield of 40% of theory.

EXAMPLE 11

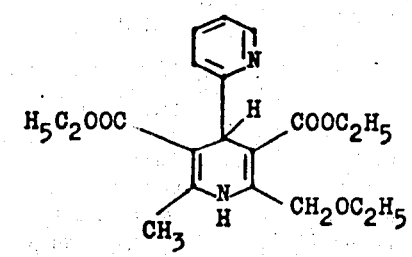

7.5 g of pyridin-2-aldehyde, 15 g of γ-ethoxyacetoacetic acid ethyl ester and 9.1 g of β-aminocrotonic acid ethyl ester in 60 ml of ethanol are heated to the boil for 5–6 hours and after cooling and filtration 2-ethoxymethyl-6-methyl-4-α-pyridyl-1,4-dihydropyridine-3,5-dicarboxylic acid diethyl ester is obtained in the form of light yellow crystals of melting point 135°C, in a yield of 35% of theory.

EXAMPLE 12

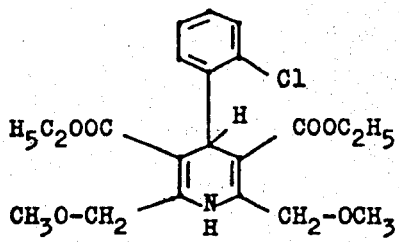

A solution of 14 g of 2-chlorobenzaldehyde, 32 g of γ-methoxyacetoacetic acid ethyl ester and 10 ml of aqueous concentrated ammonia in 60 ml of ethanol is heated to the boil overnight, and after filtration 2,6-dimethoxymethyl-4-(2'-chlorophenyl)-1,4-dihydropyridine-3,5-dicarboxylic acid ethyl ester is obtained in the form of light yellow crystals of melting point 133°–134°C, in a yield of 55% of theory.

EXAMPLE 13

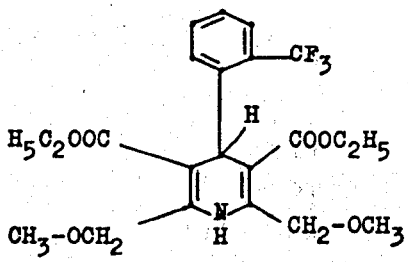

8.7 g of 2-trifluoromethylbenzaldehyde, 16 g of γ-methoxyacetoacetic acid ethyl ester and 5 ml of aqueous concentrated ammonia in 30 ml of ethanol are heated to the boil overnight, the mixture is cooled and 2,6-dimethoxymethyl-4-(2'-trifluoromethylphenyl)-1,4-dihydropyridine-3,5-dicarboxylic acid diethyl ester is obtained in the form of light brown crystals of melting point 133°–134°C, in a yield of 60% of theory.

EXAMPLE 14

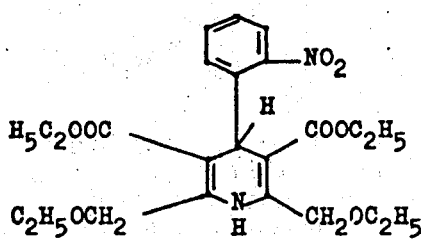

A solution of 15 g of 2-nitrobenzaldehyde, 35 g of γ-ethoxyacetoacetic acid ethyl ester and 11 ml of aqueous concentrated ammonia in 80 ml of ethanol is heated to the boil overnight and then cooled. After filtration, 2,6-(diethoxy-methyl)-4-(2'-nitrophenyl)-1,4-dihydropyridine-3,5-dicarboxylic acid diethyl ester is obtained in the form of yellow crystals of melting point 138°–140°C, in a yield of 50% of theory.

EXAMPLE 15

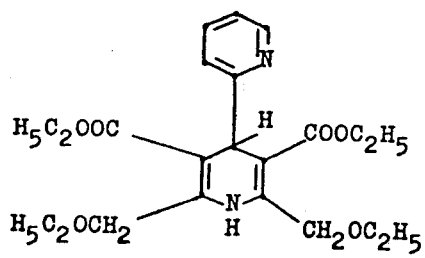

5.2 ml of pyridin-2-aldehyde, 17.4 g of γ-ethoxyacetoacetic acid ethyl ester and 5 ml of aqueous concentrated ammonia in 40 ml of ethhanol are heated to the boil overnight, the mixture is cooled, the product is filtered off, the crystals obtained (melting point 110°C) are dissolved in ether and the HCl salt is precipitated with ethereal hydrogen chloride. The hydrochloride of 2,6-(diethoxymethyl)-4-α-pyridyl-1,4-dihydrpyridine-3,5-dicarboxylic acid diethyl ester, of melting point 168°–170°C, is obtained.

Yield: 45% of theory.

EXAMPLE 16

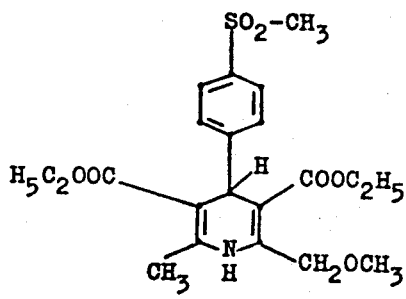

A solution of 9.2 g of 4-methylsulphonylbenzaldehyde, 8 g of γ-methoxyacetoacetic acid ethyl ester and 6.5 g of β-aminocrotonic acid ethyl ester in 40 ml of ethanol is heated to the boil and, after cooling, 2-methoxymethyl-6-methyl-4-(4'-methylsulphonylphenyl)-1,4-dihydropyridine-3,5-dicarboxylic acid diethyl ester is obtained in the form of yellow crystals of melting point 156°–158°C.

Yield: 65% of theory.

EXAMPLE 17

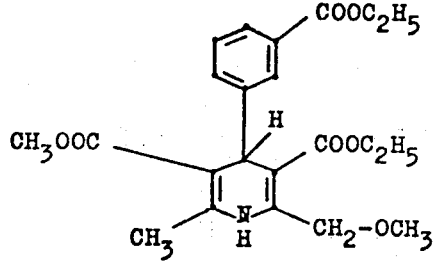

After heating a solution of 8.9 g of 3-carbethoxybenzaldehyde, 8 g of γ-methoxyacetoacetic acid ethyl ester and 6 g of β-aminocrotonic acid methyl ester in 30 ml of ethanol for several hours, 2-methoxymethyl-6-methyl-4-(3'-carbethoxyphenyl)-1,4-dihydropyridine-3-carboxylic acid methyl ester-5-carboxylic acid ethyl ester is obtained in the form of light yellow crystals of melting point 108°–110°C.

Yield: 60% of theory.

EXAMPLE 18

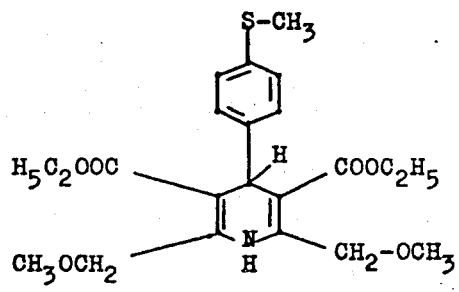

7.6 g of 4-methylmercaptobenzaldehyde, 16 g of γ-methoxyacetoacetic acid ethyl ester and 6 ml of aqueous concentrated ammonia in 30 ml of ethanol are heated to the boil for 6–8 hours, and 2,6-dimethoxymethyl-4-(4'-methylmercaptophenyl)-1,4-dihydropyridine-3,5-dicarboxylic acid diethyl ester is obtained in the form of beige crystals of melting point 136°–138°C.

Yield: 50% of theory.

a. The same compound, of melting point 137°–138°C, is obtained when 7.6 g of 4-methylmercaptobenzaldehyde and 16 g of β-amino-γ-methoxycrotonic acid ethyl ester in 40 ml of ethanol are heated to the boil overnight.

EXAMPLE 19

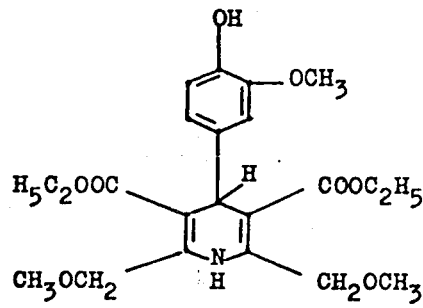

7.6 g of 3-methoxy-4-hydroxybenzaldehyde, 16 g of γ-methoxymethylacetoacetic acid ethyl ester and 12 ml of aqueous concentrated ammonia in 30 ml of ethanol are heated to the boil overnight, and after cooling 2,6-dimethyoxymethyl-4-(3'-methoxy-4'-hydroxyphenyl)-1,4-dihydropyridine-3,5-dicarboxylic acid diethyl ester is obtained in the form of light yellow crystals of melting point 140°–142°C, in a yield of 40% of theory.

EXAMPLE 20

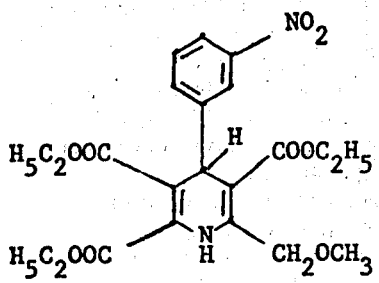

After heating a solution of 15.1 g of 3-nitrobenzaldehyde, 16 g of β-amino-γ-methoxycrotonic acid ethyl ester and 19 g of oxalacetic acid diethyl ester in 60 ml of ethanol under reflux for 12 hours, the mixture is evaporated in vacuo and 2-methoxymethyl-4-(3'-nitrophenyl)-1,4-dihydropyridine-3,5,6-tricarboxylic acid triethyl ester is obtained in almost quantitative yield, in the form of a yellow oil ($n_D^{50}$ =1.5353).

EXAMPLE 21

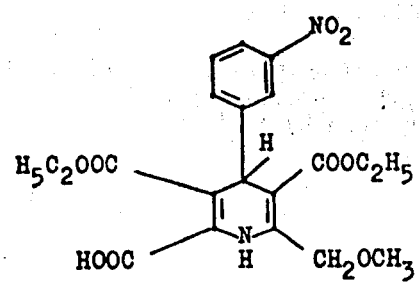

After addition of a solution of 1.15 g of sodium in 25 ml of ethanol, 23 g of the triester obtained according to Example 20 are heated, in a total of 200 ml of ethanol, to the boil overnight, the mixture is then concentrated in vacuo the residue is taken up in water, and after filtration the product is precipitated with dilute sulphuric acid. 2-Methoxymethyl-4-(3'-nitrophenyl)-1,4-dihydropyridine-3,5-dicarboxylic acid diethyl ester-6-carboxylic acid is obtained in the form of yellow crystals of melting point 146°C, in a yield of 50% of theory.

EXAMPLE 22

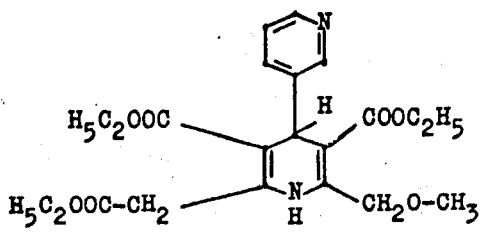

A solution of 10.2 ml of pyridin-3-aldehyde, 16 g of γ-methoxyacetoacetic acid ethyl ester and 20 g of β-iminoglutaric acid ethyl ester in 40 ml of ethanol is heated to the boil overnight and then cooled. After cooling, 2-methoxymethyl-4-(β-pyridyl)-1,4-dihydropyridine-3,5-dicarboxylic acid diethyl ester-6-acetic acid ethyl ester is obtained in the form of light yellow crystals of melting point 104°–106°C, in a yield of 65% of theory.

EXAMPLE 23

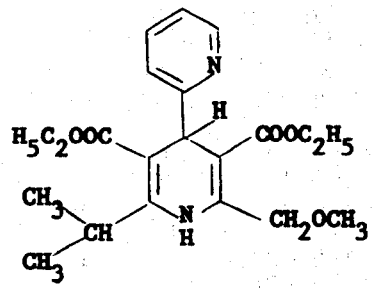

A solution of 5.2 ml of pyridin-2-aldehyde, 8 g of isobutyroylacetic acid ethyl ester and 8 g of β-amino-γ-methoxycrotonic acid ethyl ester (boiling point 112°–116°/10 mm) in 40 ml of ethanol is heated to the boil overnight and is concentrated, the residue is taken up in ether and 2-methoxymethyl-6-isopropyl-4-(α-pyridyl)-1,4-dihydropyridine-3,5-dicarboxylic acid diethyl ester is precipitated, as the hydrochloride, by means of ethereal hydrochloric acid.

Light yellow crystals of melting point 198°–200°C. Yield: 60%.

EXAMPLE 24

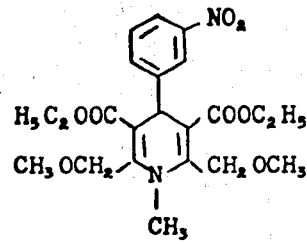

7.5 g of 3-nitrobenzaldehyde, 16 g of γ-methoxyacetoacetic acid ethyl ester and 5 g of methylamine hydrochloride in 40 ml of pyridine are heated to 90°–100°C for 5-6 hours, the mixture is concentrated in vacuo, the residue is taken up in ether, and the ethereal solution is washed with dilute hydrochloric acid and with water, dried and evaporated.

1-Methyl-2,6-dimethoxymethyl-4-(3'-nitrophenyl)-1,4-dihydropyridine-3,5-dicarboxylic acid diethyl ester is obtained as a brown oil, in 90% yield.

What is claimed is:

1. A compound selected from the group consisting of a dihydropyridine of the formula:

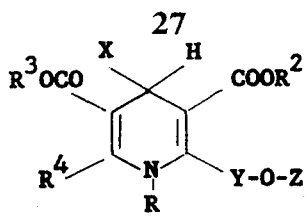

and the pharmaceutically acceptable nontoxic salts thereof wherein

Y is alkylene of 1 to 4 carbon atoms;

Z is alkyl of 1 to 4 carbon atoms;

R is hydrogen, alkyl of 1 to 4 carbon atoms, or alkenyl of 2 to 4 carbon atoms; each of $R^2$ and $R^3$, independent of the other, is alkyl of 1 to 6 carbon atoms, alkenyl of 2 to 6 carbon atoms, alkynyl of 2 to 6 carbon atoms or cycloalkyl of 3 to 10 carbon atoms;

$R^4$ is hydrogen, alkyl of 1 to 6 carbon atoms, Z-O-Y- wherein Z and Y are as defined above, or carbalkoxymethyl; and X is unsubstituted or substituted by dialkylamino of 1 to 4 carbon atoms in each alkyl group, or pyridyl.

2. A compound according to claim 1 wherein X is pyridyl or pyrimidyl.

3. A compound according to claim 2 wherein
R is hydrogen; and
Y is methylene.

4. A compound according to claim 3 wherein
Z is methyl, ethyl, propyl or isopropyl;
each of $R^2$ and $R^3$ are independently methyl or ethyl; and
$R^4$ is methyl, ethyl, propyl, isopropyl, methoxymethyl or ethoxymethyl.

5. A compound according to claim 1 which is 2-isopropoxymethyl-6-methyl-4-α-pyridyl-1,4-dihydropyridine-3,5-dicarboxylic acid ethyl ester.

6. A compound according to claim 1 which is 2-ethoxymethyl-6-methyl-4-(2'-dimethylaminopyrimidyl)-1,4-dihydropyridine-3,5-dicarboxylic acid diethyl ester.

7. A compound according to claim 1 which is 2-ethoxymethyl-6-methyl-4-α-pyridyl-1,4-dihydropyridine-3,5-dicarboxylic acid diethyl ester.

8. A compound according to claim 1 which is the hydrochloride of 2,6-(diethoxymethyl)-4-α-pyridyl-1,4-dihydropyridine-3,5-dicarboxylic acid diethyl ester.

9. A compound according to claim 1 which is 2-methoxymethyl-4-(β-pyridyl)-1,4-dihydropyridine-3,5-dicarboxylic acid diethyl ester-6-acetic acid ethyl ester.

10. A compound according to claim 1 which is 2-methoxymethyl-6-isopropyl-4-(α-pyridyl)-1,4-dihydropyridine-3,5-dicarboxylic acid diethyl ester.

11. A pharmaceutical composition which comprises a coronary vessel dilating amount of a compound claim 1 in combination with an inert pharmaceutically acceptable carrier.

12. A method for effecting coronary vessel dilation which comprises administering an effective amount of a compound according to claim 1.

* * * * *